Figure 1:
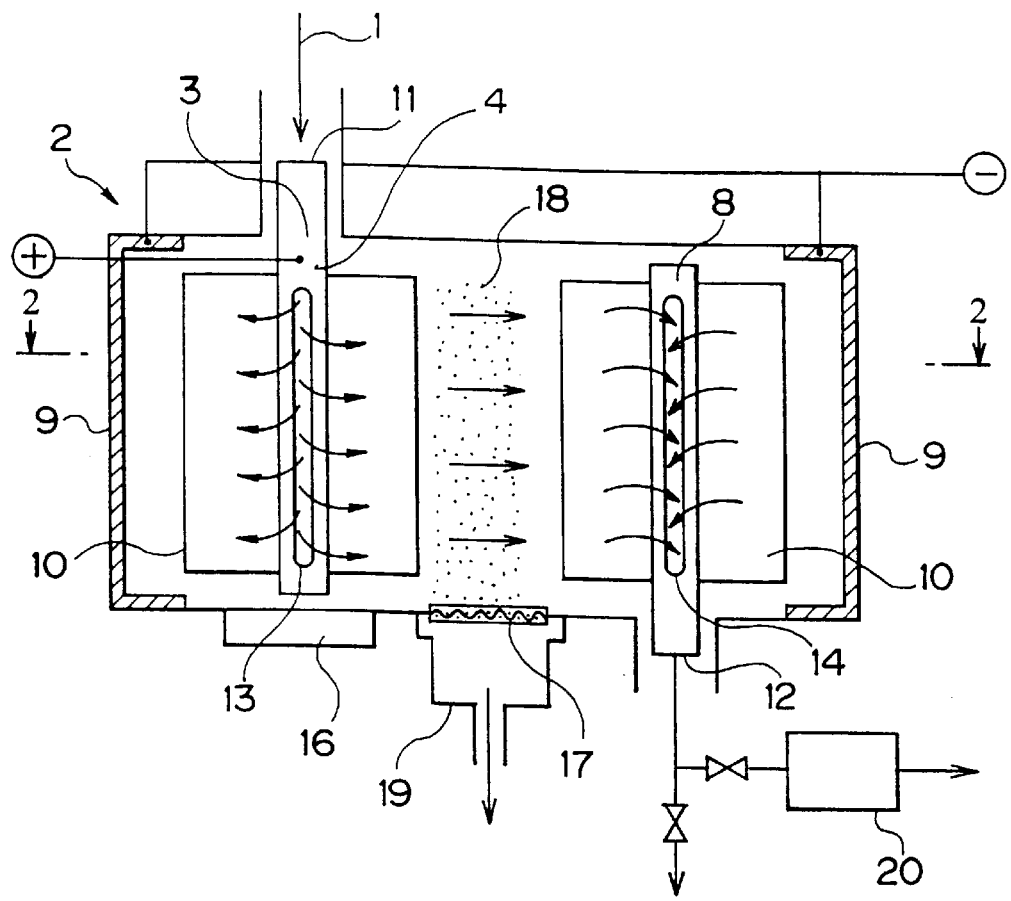
Figure 2:
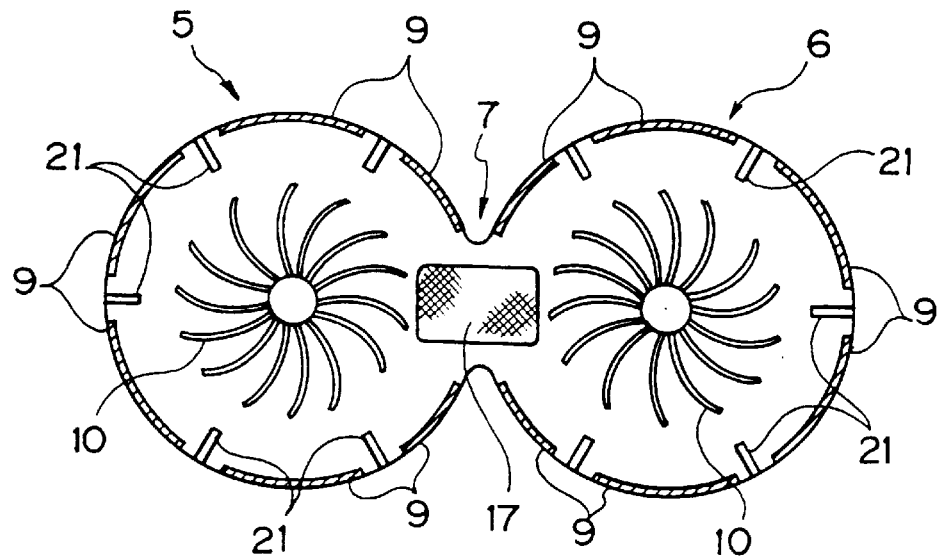
Figure 3:
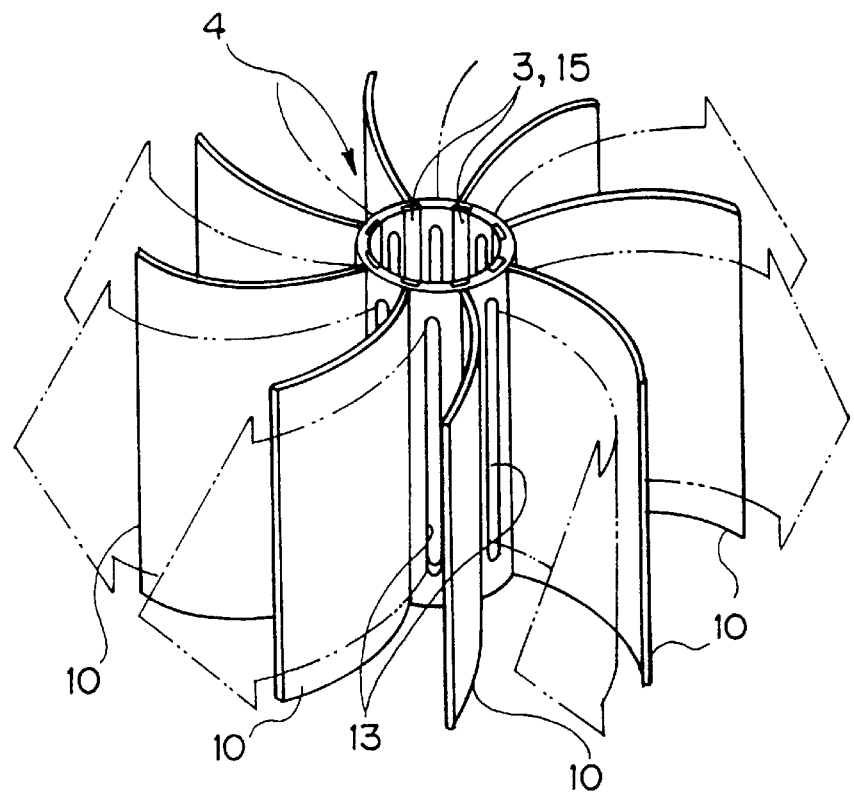
Figure 4:
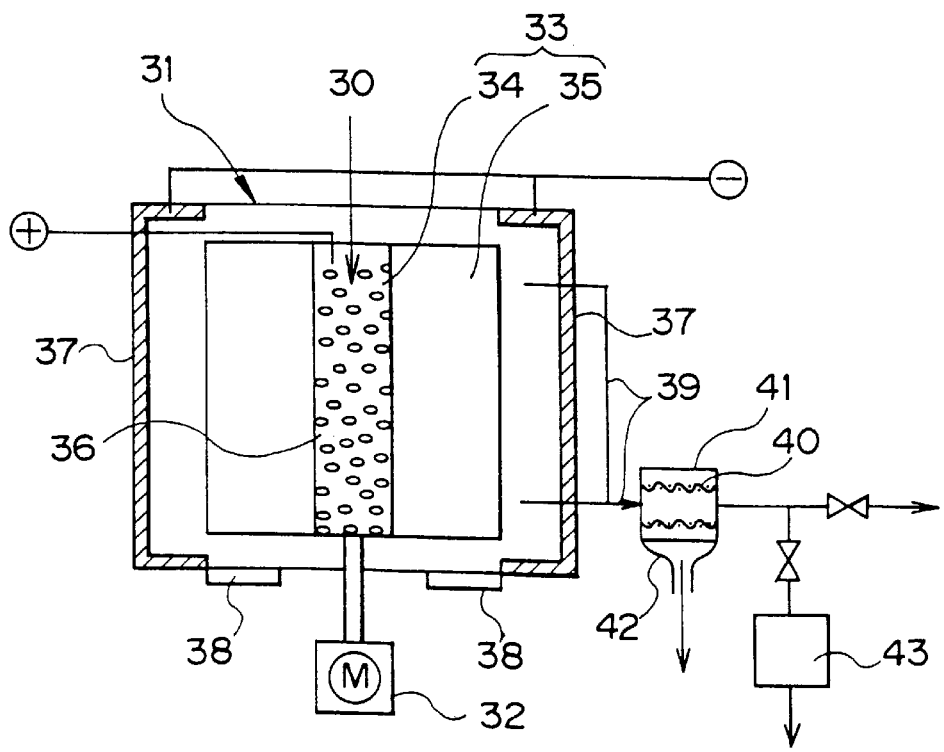

United States Patent [19]
Yoshida et al.

[11] Patent Number: 5,948,273
[45] Date of Patent: *Sep. 7, 1999

[54] WATER PURIFICATION PROCESS AND APPARATUS

[75] Inventors: Kanji Yoshida; Teruaki Sumioka, both of Kumamoto-ken; Haitao Xu, Saitama-ken, all of Japan

[73] Assignees: Remodeling 21 Co., Ltd., Tokyo; Kanji Yoshida, Kumamoto-ken, both of Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/580,906

[22] Filed: Dec. 29, 1995

[30] Foreign Application Priority Data

Oct. 17, 1995 [JP] Japan ..................................... 7-268885

[51] Int. Cl.$^6$ .................................................. B01D 17/06
[52] U.S. Cl. .............................. 210/748; 210/764; 422/20
[58] Field of Search ..................................... 210/748, 764; 422/20

[56] References Cited

U.S. PATENT DOCUMENTS

| | | | |
|---|---|---|---|
| 3,650,094 | 3/1972 | Goodwin | 210/748 |
| 4,957,606 | 9/1990 | Juvan | 210/748 |
| 5,094,734 | 3/1992 | Torrado | 210/754 |

FOREIGN PATENT DOCUMENTS

| | | |
|---|---|---|
| 0468478 | 1/1992 | European Pat. Off. . |
| 3708947 | 9/1988 | Germany . |
| 4150992 | 5/1992 | Japan . |

*Primary Examiner*—Jay H. Woo
*Assistant Examiner*—Betsey J. Morrison
*Attorney, Agent, or Firm*—McDermott, Will & Emery

[57] ABSTRACT

A water purification process comprises applying electrical energy to water to be treated in a treatment chamber having a cathode and an anode opposing each other and deactivates or destroys microorganisms in the water. Water in the vicinity of the anode is caused to flow away from the anode by subjecting the water and/or the anode to vibration. The water purification apparatus includes a treatment chamber (2) having a cathode (9) and an anode (3) opposing each other. Electrical energy is applied to microorganisms contained in the water. The anode and/or the water in the vicinity of the anode is vibrated and debris inside and outside the chamber is removed (17).

15 Claims, 3 Drawing Sheets

WATER PURIFICATION PROCESS AND APPARATUS

FIELD OF THE INVENTION

The present invention relates to water purification process and apparatus which deactivates or destroy microorganisms, for the purpose of bacteriolysis, virolysis, disinfection or sterilization.

BACKGROUND OF THE INVENTION

Various processes have been developed and proposed to perform bacteriolysis, disinfection and sterilization by efficiently destroying microorganisms including bacteria such as *Pseudomonas aeruginosa* and *Escherichia coli* and other Eumycetes, and minute viruses. However, none of these known processes has adequately considered the properties of microorganisms. For example, electrochemical sterilization is premised on bringing the microorganisms into contact with an electrode surface or dielectric substance, to inhibit their biochemical reactions. The surface of a bacteria typically has a negative charge and is attracted to a positive electrode, and is destroyed by contact. However, when the number of bacteria increases, they exhibit a state in which protoplasm accumulates inside the bacteria, that protects the bacteria with protein. They thus effectively have an electrical shield. Tois causes a decrease in bactericidal function which makes maintenance and management of the electrodes susceptible to the occurrence of problems. As a result, practical application is correspondingly difficult.

SUMMARY OF THE INVENTION

This invention is based on a consideration of the mechanism by which microorganisms are destroyed. It has been found that, when bacteria are destroyed, they emit cytoplasm prior to contact with a positive electrode. Bacteria can be considered to be microcapacitors; their cell membrane is destroyed when they are subjected to an electric charge in an electric field, and that charge exceeds the electrostatic capacity.

A water purification process according to the present Invention comprises introducing water to be treated into a treatment chamber having a cathode and an anode opposing each other, and applying electrical energy to deactivate or destroy microorganisms in the water. At the same time, steps are taken to prevent contact between the anode and the microorganisms and between the anode and the deactivated or destroyed substances. The water in the vicinity of the anode is caused to flow away from the anode by vibrating the water in the vicinity of the anode and/or by vibrating the anode. Deactivated or destroyed substances, including debris, produced as a result of the treatment, are then removed both inside and outside the chamber, to give purified water.

By means of the present invention, since destruction of the cell membrane is caused by applying electrical energy under circumstances where the microorganisms do not make contact with an anode, problems caused by contact with debris and the microorganisms with the anode can be avoided. In particular, decreases In anode efficiency can be prevented. Moreover, since maintenarce and management of the electrodes are correspondingly easier, there is no decrease in bactericidal efficiency. Accordingly, the present process and apparatus are advantageous in that the amount of electricity required for applying electrical power may be small. Large volumes of water can be purified. Semi-pure water can also be obtained, if desired.

Impurities in the water may be removed by passing the purified water to a high-purity filter. In the water purification process itself, powerful electrical energy is applied to the microorganisms, and bubbles of gas produced in the water to be treated may be broken by separately applying ultrasonic waves to the aqueous solution.

Water purification apparatus according to the present Invention comprises a treatment chamber having a cathode and an anode opposing each other; means for applying electrical energy to microorganisms contained in the water; means for vibrating the water in the vicinity of the anode and/or the anode; and means for removing debris Inside and outside the chamber.

DESCRIPTION OF THE INVENTION

The water purification apparatus may also contain a flow device for the aqueous solution to be treated using a revolving anode. The debris removal means in the apparatus is preferably a single anode mesh or anode filter or a combination thereof, disposed inside and outside the treatment chamber. The solution-vibrating means in the apparatus may comprise an ultrasonic vibrator arranged near the anode. The anode-vibrating means may comprise a vibrator connected to an electrode case equipped with an anode and cathode. The flow means, solution-vibrating means, anode-vibrating means, debris removal means and high-purity filter as described above are used In combination.

The present invention aims at explosively destroying the membrane of microorganism cells by applying electrical energy to the microorganisms via a liquid, In an electric field, to promote osmosis inside and outside the microorganism cells. While an example of the use of a liquid having an electric field involves applying current to the micrcorganisms-ccntaining liquid Itself, by means of an electrode, the electrode and the microorganisms to which electrical energy is applied are not in contact. The means of apolying current may be via either a conductive or nonconductive medium.

In this specification, the term "water to be treated" refers to a solution containing microorganisms such as bacteria or minute viruses, such as tap water and other drinking water, washing water for sterilizing the hands and feet, cold and hot bath water, pool water, and cleaning water for cleaning industrial products. Thus, the term "water to be treated" is used in a broad sense as a generic term for the medium required to deactivate or destroy microorganisms. The "electrical energy" that is applied may be varied from low to high or weak to strong intensity, and is set according to the volume of water to be treated for purification, the size of the purification apparatus and other conditions.

The term "purification" is used as a conceptual term including bacteriolysis, virolysis, disinfection and sterilization of microorganisms and the removal of organic impurities.

The term "cell membrane" is used in the broad sense, and refers generically to the boundary membrane, external membrane, interfacial membrane, protoplasmic membrane or cell wall that separates the protoplasm of the cell from the outside.

The term "explosively destroying" as used herein refers directly to the states where-strong membrane contraction occurs, the cell membrane having high strong elasticity, such that the cell contents (protoplasm) spray out and scatter radially in all directions; where the cell membrane has low elasticity and the internal pressure of the cell is high, such that local destruction of the cell membrane occurs, causing translational spraying with little peripheral scattering; or where the cell membrane has weak elasticity and external pressure is relatively low, such that translational spraying and peripheral scattering occur. The same term is also used in the broad sense, to refer generically to destruction, including turgor pressure destruction as well as lysis, dehydration, coagulation, melting, perforation and so forth, which are typical phenomena of bacterial destruction.

The term "charged water" is used herein to refer generically to charging water, battery water, functional water, electrolysis treatment water, high oxidation potential water, strongly acidic electrolytic regeneration aqueous solution, ionized water, non-ionized water, or electrified water. The phrase "applying current" is not limited to the application of current via a conductive medium, e.g. a solution of a conductive substance such as NaCl, but also includes the application of current via a liquid that is not generally supposed to be conductive, such as purified water. It has been confirmed that when current is applied after viable microorganisms are suspended in purified water, a current is obtained that is smaller than that in a conductive medium. This is apparently the result of a jumping conductivity effect (a type of non-conductive medium current flow) that exists between microorganisms, by which microorganisms form a constant flow in the direction of the positive electrode.

The term "osmosis" refers to the phenomenon of water in solution moving towards the higher concentration side when divided by a water-permeable solute-impermeable membrane If the osmotic pressure is increased, it causes destruction of the cell membrane. The term "irreversible change" is used to refer generically to states in which the cell membrane inhibits the transport of substances, the cell membrane Itself is changed or modified, or the protoplasm is changed or modified.

The invention will now be described, by way of example only, with reference to the the apparatus illustrated in the accompanying drawings, in which:

FIG. 1 is a schematic sectional side view of water purification apparatus that is a first embodiment of the present Invention;

FIG. 2 is a schematic cross-secticnal view along the line A—A of FIG. 1;

FIG. 3 is a perspective view showing a partial cross-section of the revolving body of FIG. 1;

FIG. 4 is a schematic sectional side view of water purification apparatus that is second embodiment of the present invention;

FIG. 5 is a schematic sectional plan view of water purification apparatus that is a third embodiment of the present invention; and FIG. 6 is a schematic cross-sectional view of debris removal means, along the line B—B of FIG. 5.

FIGS. 1 to 3 show water purification apparatus equipped with an anode 3 in the form of a revolving body 4 in a treatment chamber 2 for continuous treatment of water 1 to be treated, under positive flow. As shown in FIG. 2, a treatment chamber 2 comprises left and right cylindrical portions 5 and 6 connected by a central narrow portion 7. Revolving bodies 4 and 8 are arranged such that they can revolve freely in the centres of cylindrical portions 5 and 6, respectively. A plurality of cathodes 9 are arranged around the periphery at locations so as to surround the revolving bodies 4 and 8. The flow of water impinges on baffle plates 21 within the treatment chamber 2 and surrounding mainly the periphery of anode 3.

A plurality of curved fins 1n are attached to the cylindrical shaft portions of revolving bodies 4 and 8. The revolving body 4 is equipped with a feed inlet 11 for introducing the water 1 to be treated. The revolving body 8 is equipped with a discharge outlet 12 for discharging purified water. A plurality of slits 13 for water input are formed In the shaft of revolving body 4. Water discharge slits 14 are formed In the shaft of the other revolving body 8. The revolving body 4 functions as the anode 3, and first anode plates 15 made of platinum are attached inside the shaft as insoluble anodes. The fins 10 are made of titanium, and serve as second anode plates.

The revolving body 4 provides means whereby water to be treated in the vicinity of anode 3 is caused to flow away in a direction away from the anode 3.

An ultrasonic vibrator 16 and an anode mesh 17 are provided on the bottom of the treatment chamber 2. The ultrasonic vibrator 16 is located near the revolving body 4/anode 3. This vibrator applies vibrations to the water to be treated in the vicinity of anode 3; it also destroys bubbles of gas produced in the water as electrical energy is applied by the current between the cathode 9 and the anode 3.

An anode mesh 17 serves to remove debris. It is arranged on the bottom of a narrow portion 7 between the cylindrical portions 5 and 6. A large amount of debris 18 is produced when microorganisms are deactivated or destroyed. The anode mesh 17 captures this debris during flow from left to right in FIGS. 1 and 2. Debris is discharged and removed via a debris drain 19. Following removal of debris, the purified water is either removed as such or further purified by passage to a high-purity filter 20 and then removed.

The treatment chamber 2 can be substantially provided and connected in plural as a single unit, which can further improve purifying efficiency.

FIG. 4 shows apparatus aimed at performing intermittent treatment (so-called batch treatment). An anode 33 is provided In a treatment chamber 31 and is rotated by a motor 32 to cause positive flow of water 30 to be treated. The anode 33 is provided in the form of a revolving body, and is formed by integrating a cylindrical shaft 34 and fins 35 into a single unit using an Insoluble anodic metal. A large number of spray ports 36 are arranged in the cylindrical shaft 34, A plurality of cathodes 37 are provided at locations so as to surround the periphery of this anode 33 on the walls of treatment chamber 31. The revolving anode 33 causes water to be treated in the vicinity of anode 33 to flow away from the anode 33.

An ultrasonic vibrator 38 is disposed on the bottom of the treatment chamber 31, and is located near the anode 33. The vibrator 38 applies vibrations to the water to be treated in the vicinity of anode 33, and also destroys bubbles of gas that may be produced if a high level of electrical energy is applied to the microorganisms.

A discharge tube 39 is connected to the treatment chamber 31, and contains a debris removal means in the form of anode mesh 40. This anode mesh 40 is adapted to positive removal of debris 41 from the water. The anode mesh 40 is disposed within a horizontal cylindrical case 41 so that the debris is attracted to the anode mesh 40 as the water to be treated flows through the case 41, after which that debris is discharged via a debris drain 42. While purified water following removal of debris 41 may be discharged as such, it may also be discharged in the form of seri-pure water by removing impurities as a result of additionally applying it to a high-purity filter 43.

According to both the first and second embodiments, water 30 to be treated in the vicinity of anode flows in a direction away from the anode 33. Since current flows through the water 30 to be treated that has filled the inside of the treatment chamber 31 between the cathode 37 and the anode 33, electrical energy Is applied to the microorganisms in the water 30 to be treated. Osmosis inside and outside the cell membrane may thus be promoted, so that the cell membrane is explosively destroyed, the cells collapse, cytoplasm (protoplasm) Is released, and a large number of microorganisms are substantially completely deactivated or destroyed.

A large amount of debris 41 is produced as a result of this deactivation or destruction. The debris 41 and other materials are mixed in the water. However, since the materials do not approach the anode 33, as a result of being stirred by the revolving body, but rather flow in a direction away from the anode 33, the debris 41 is captured by the anode mesh 40, and is discharged and removed via the debris drain 42.

The phenomena of deactivation and destruction of microorganisms occur without contact with the anode 33. Due to the flow of water created by the revolving body and/or by the ultrasonic vibrator 38, contact between the anode 33 and microorganisms as well as that between the anode 33 and the debris 41 is prevented. Since the debris 41 is scattered by the revolving body, problems resulting from its contact with the anode 33 can be avoided. There is thus no decrease in anode efficiency. Thus, maintenance and management of the electrodes are correspondingly easier, thereby enabling a large volume of water to be treated and purified.

Microorganisms, which can be considered to be capacitors, are destroyed when they are subjected to an electrical charge. When their electrostatic capacity is exceeded, the cell membrane is destroyed, purification of water is achieved by deactivation or destruction of microorganisms without using electrical energy that is more powerful than that required for destruction. If a high level of electrical energy is applied. e.g. to microorganisms having a particularly tough cell membrane, by applying a large current and large voltage between the cathode 37 and the anode 33, bubbles of gas produced in the aqueous solution to be treated are efficiently destroyed by the ultrasonic vibrator 38 and deactivation or destruction of microorganisms adhering to those bubbles is promoted.

Introduction, purification and discharge of water can be performed continuously. It should be noted that the removed purified water can also be applied to the high-purity filter 20 to enable it to be removed as semi-pure water having a high degree of purity. This semi-pure water Is particularly suitable as cleaning water for industrial products.

Figure 5:
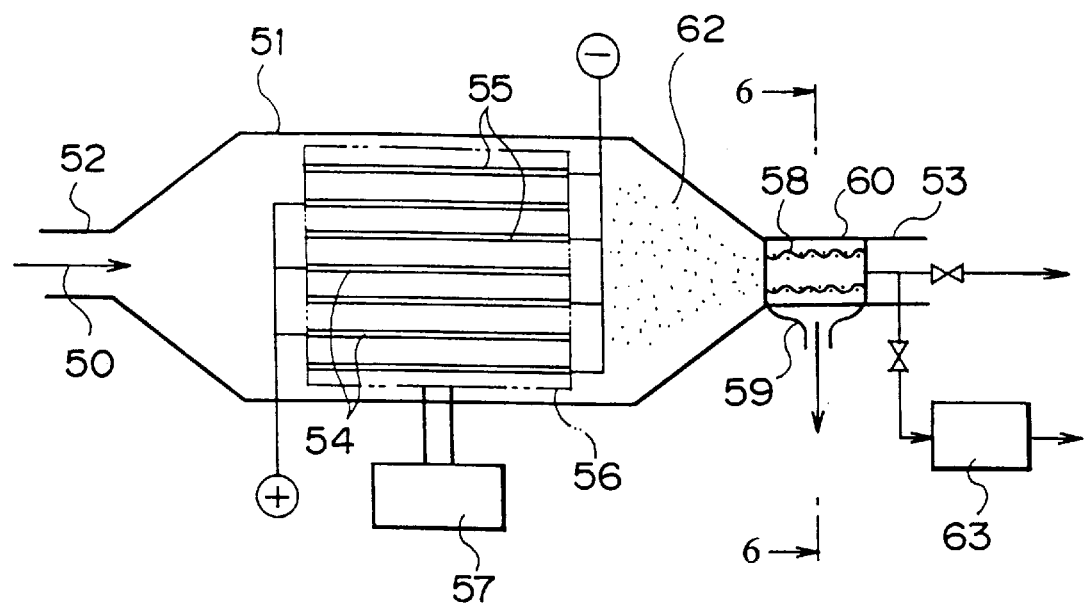
Figure 6:
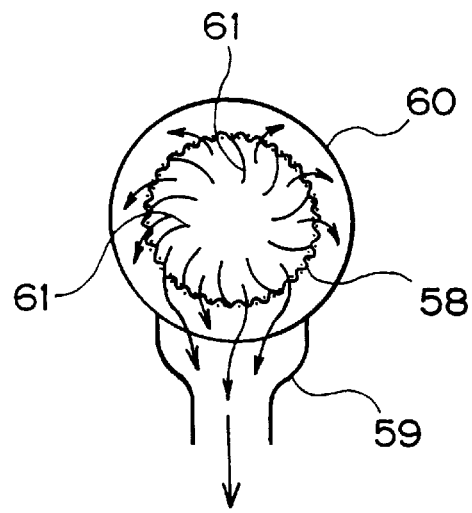

FIGS. 5 and 6 snow water purification apparatus aimed at continuous treatment. A treatment chamber 51 has an inlet 52 and an outlet 53 that are coaxial, for a positive flow of water 50 to be treated. An electrode case 56, in which a large number of anodes 54 and cathodes 55 are alternately arranged, Is incorporated within the treatment chamber 51. A vibrator 57 is connected to this electrode case 56. A debris drain 59 combined with a debris removal means in the form of an anode filter 58 is provided in the vicinity of the discharge outlet 53. Within the case 60, the anode filter 58 is combined with rectifying vanes 61 arranged in spiral fashion. Positive flow of water containing a large amount of debris causes the debris 62 to make contact with the anode filter 58; efficient removal of debris is achieved. A high-purity filter 63 is also provided.

Electrical energy is applied during that time of passage of water 50 to be treated through the chamber 51, resulting in deactivation or destruction of microorganisms in the water to be treated. The solution then flows as such in a direction away from the anodes 54, thereby preventing contact between the debris 62 and the anodes 54. Moreover, since the vibrator 57 vibrates the electrode case 56, the microorganisms and the debris 59 also do not make contact with the anodes 54. Thus, problems resulting from their contact with the anodes 54 can be avoided. There is thus no decrease In anode efficiency, and maintenance and management of the electrodes are correspondingly easier.

The flow rate of the water SO to be treated can be easily controlled with a valve (not shown). The application of electrical energy to the microorganisms can be controlled corresponding to the flow rate. Other factors are described in connection with the first and second embodiments.

We claim:

1. A water purification process comprising applying electrical energy to water to be treated in a treatment chamber having at least one cathode and at least one anode opposing each other, to deactivate or destroy microorganisms in the water, the process further comprising:

causing water to flow away from the at least one anode by vibrating said at least one anode.

2. A process according to claim 1, which further comprises removing impurities and/or debris from said water by means of a high-purity filter.

3. A process according to claim 1, wherein bubbles of gas produced by applying electrical energy to the water are broken by applying ultrasonic waves to the water or vibrating the electrodes.

4. A process according to claim 2, wherein bubbles of gas produced by applying electrical energy to the water are broken by applying ultrasonic waves to the water or vibrating the electrodes.

5. A process according to claim 1, wherein introduction and discharge of the water to be treated is performed continuously in the treatment chamber.

6. A process according to claim 2 wherein introduction and discharge of the water to be treated is performed continuously in the treatment chamber.

7. A process according to claim 3, wherein introduction and discharge of the water to be treated is performed continuously in the treatment chamber.

8. A process according to claim 4, wherein introduction and discharge of the water to be treated is performed continuously in the treatment chamber.

9. A process according to claim 1, wherein introduction and discharge of the water to be treated is performed intermittently in the treatment chamber.

10. A process according to claim 2, wherein introduction and discharge of the water to be treated is performed intermittently in the treatment chamber.

11. A process according to claim 3, wherein introduction and discharge of the water to be treated is performed intermittently in the treatment chamber.

12. A process according to claim 4, wherein introduction and discharge of the water to be treated is performed intermittently in the treatment chamber.

13. A process according to claim 1, wherein bubbles of gas produced by applying electrical energy in the water are broken by applying ultrasonic waves to the water and vibrating the electrodes.

14. A process according to claim 2, wherein bubbles of gas produced by applying electrical energy in the water are broken by applying ultrasonic waves to the water and vibrating the electrodes.

15. A water purification process comprising applying electrical energy to water to be treated in a treatment chamber having at least one cathode and at least one anode opposing each other, to deactivate or destroy microorganisms in the water, the process further comprising causing water to flow away from the at least one anode by rotating said at least one anode.

* * * * *

UNITED STATES PATENT AND TRADEMARK OFFICE
CERTIFICATE OF CORRECTION

PATENT NO.    : 5,948,273
DATED         : September 7, 1999
INVENTOR(S)   : KANJI YOSHIDA, et al.

It is certified that error appears in the above-identified patent and that said Letter Patent is hereby corrected as shown below:

Column 3, line 42, change "A-A" to --2-2--;

line 52, change "B-B" to --6-6--.

Signed and Sealed this

Sixth Day of June, 2000

Q. TODD DICKINSON

*Attest:*

*Attesting Officer*     *Director of Patents and Trademarks*